(12) United States Patent
Cao et al.

(10) Patent No.: US 11,644,583 B2
(45) Date of Patent: *May 9, 2023

(54) X-RAY DETECTORS OF HIGH SPATIAL RESOLUTION

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 72 days.

This patent is subject to a terminal disclaimer.

(21) Appl. No.: 17/307,141

(22) Filed: May 4, 2021

(65) Prior Publication Data
US 2021/0255343 A1  Aug. 19, 2021

Related U.S. Application Data

(63) Continuation of application No. 15/737,797, filed as application No. PCT/CN2015/091927 on Oct. 14, 2015, now Pat. No. 11,029,424.

(51) Int. Cl.
*G01T 1/24* (2006.01)
*H01L 27/146* (2006.01)
(Continued)

(52) U.S. Cl.
CPC ........ *G01T 1/247* (2013.01); *H01L 27/14623* (2013.01); *H01L 27/14659* (2013.01);
(Continued)

(58) Field of Classification Search
CPC ......... H01L 27/14623; H01L 27/14659; H01L 27/14676; G01T 1/247; G01T 1/2928;
(Continued)

(56) References Cited

U.S. PATENT DOCUMENTS 3,936,645 A * 2/1976 Iversen .................. B23K 26/40
250/370.11
4,208,577 A * 6/1980 Wang .................... H01J 29/385
313/526
(Continued)

FOREIGN PATENT DOCUMENTS

CN 201622252 U 11/2010
CN 102232227 A 11/2011
(Continued)

*Primary Examiner* — Irakli Kiknadze
(74) *Attorney, Agent, or Firm* — IPro, PLLC

(57) ABSTRACT

An apparatus, system and method suitable for detecting X-ray are disclosed. In one example, the apparatus comprises: an X-ray absorption layer and a mask; wherein the mask comprises a first window and a second window, and a portion between the first window and the second window; wherein the first and second windows are not opaque to an incident X-ray; wherein the portion is opaque to the incident X-ray; and wherein the first and second windows are arranged such that charge carriers generated in the X-ray absorption layer by an X-ray photon propagating through the first window and charge carriers generated in the X-ray absorption layer by an X-ray photon propagating through the second window do not spatially overlap.

12 Claims, 24 Drawing Sheets

(51) Int. Cl.
*A61B 6/00* (2006.01)
*G01N 23/046* (2018.01)
*G01V 5/00* (2006.01)
*H01J 37/244* (2006.01)

(52) U.S. Cl.
CPC ...... *H01L 27/14676* (2013.01); *A61B 6/4208* (2013.01); *G01N 23/046* (2013.01); *G01V 5/005* (2013.01); *H01J 37/244* (2013.01)

(58) Field of Classification Search
CPC ..... A61B 6/4208; A61B 6/481; A61B 6/5241; A61B 6/504; A61B 6/4291; A61B 6/484; A61B 6/4007; A61B 6/508; A61B 6/502; A61B 6/40; A61B 6/032; A61B 6/035; A61B 6/4035; A61B 6/04; A61B 6/4233; A61B 6/42; A61B 6/0407; A61B 6/0487; H01J 37/244; H01J 35/12; H01J 35/08; H01J 35/116; H01J 2235/086; H01J 35/112; H01J 2235/068; G01N 23/046; G01N 23/20075; G01N 23/041; G01N 2223/204; G01N 2223/6126; G01N 23/201; G01N 2223/419; G01N 2223/401; G01N 2223/418; G01V 5/005; G21K 1/025; G21K 1/02; G21K 2207/005; B33Y 80/00; H04N 5/3205
USPC .................................................. 378/4, 19, 62
See application file for complete search history.

(56) References Cited

U.S. PATENT DOCUMENTS

| | | | | |
|---|---|---|---|---|
| 4,433,427 A * | 2/1984 | Barnea | ................... | G21K 1/025 378/146 |
| 5,430,298 A * | 7/1995 | Possin | ................... | G01T 1/2018 250/366 |
| 5,847,398 A * | 12/1998 | Shahar | ................... | G01T 1/243 250/370.09 |
| 5,966,424 A * | 10/1999 | Liu | ................... | G21K 1/025 378/98.12 |
| 6,175,615 B1 * | 1/2001 | Guru | ................... | G21K 1/025 378/154 |
| 6,272,207 B1 * | 8/2001 | Tang | ................... | G21K 1/025 378/154 |
| 6,452,186 B1 * | 9/2002 | Wieczorek | ............ | G01T 1/2018 250/370.11 |
| 7,402,814 B2 * | 7/2008 | Vieux | ................... | H01L 27/14658 250/370.11 |
| 7,476,025 B2 * | 1/2009 | Pohan | ................... | G21K 1/02 378/205 |
| 8,586,933 B2 * | 11/2013 | Levene | ................... | G01T 1/2018 250/366 |
| 9,510,792 B2 * | 12/2016 | Wang | ................... | A61B 6/4291 |
| 11,029,424 B2 * | 6/2021 | Cao | ................... | H01L 27/14659 |
| 2004/0076319 A1 | 4/2004 | Fauver et al. | | |
| 2004/0251420 A1 * | 12/2004 | Sun | ................... | G01T 1/2018 250/370.09 |
| 2012/0263274 A1 * | 10/2012 | Ouchi | ................... | G01N 23/20075 378/62 |
| 2014/0233699 A1 * | 8/2014 | Munro | ................... | G01N 23/046 378/62 |
| 2015/0260663 A1 * | 9/2015 | Yun | ................... | H01J 35/08 378/36 |

FOREIGN PATENT DOCUMENTS

| | | |
|---|---|---|
| DE | 102004042175 A1 | 3/2006 |
| WO | 2014142236 A1 | 9/2014 |
| WO | 2014196914 A1 | 12/2014 |

\* cited by examiner

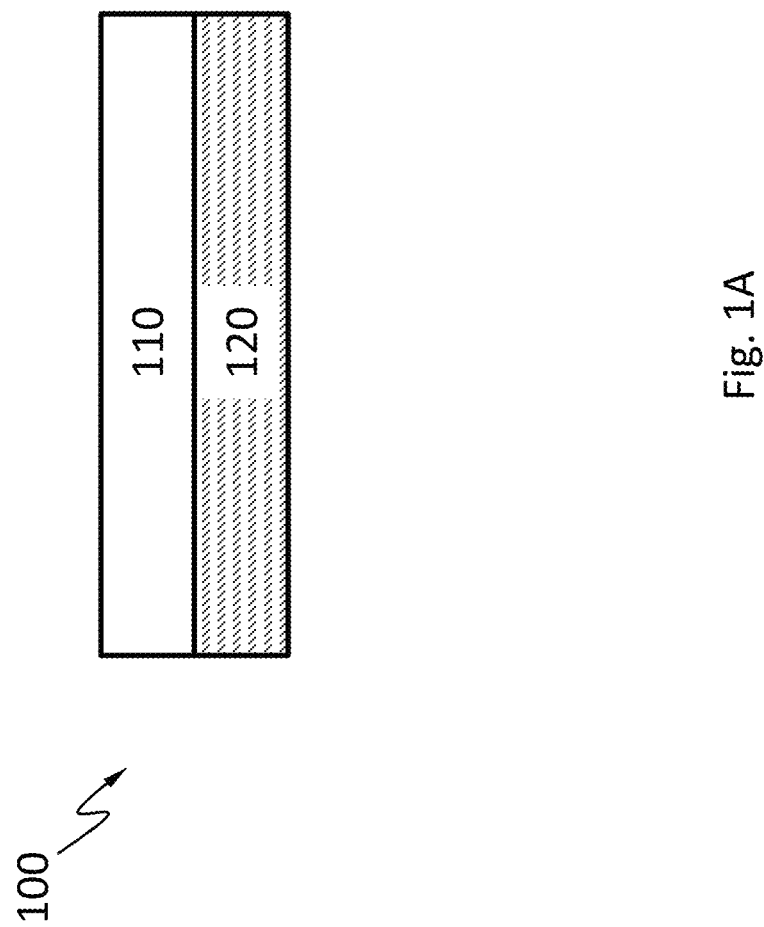

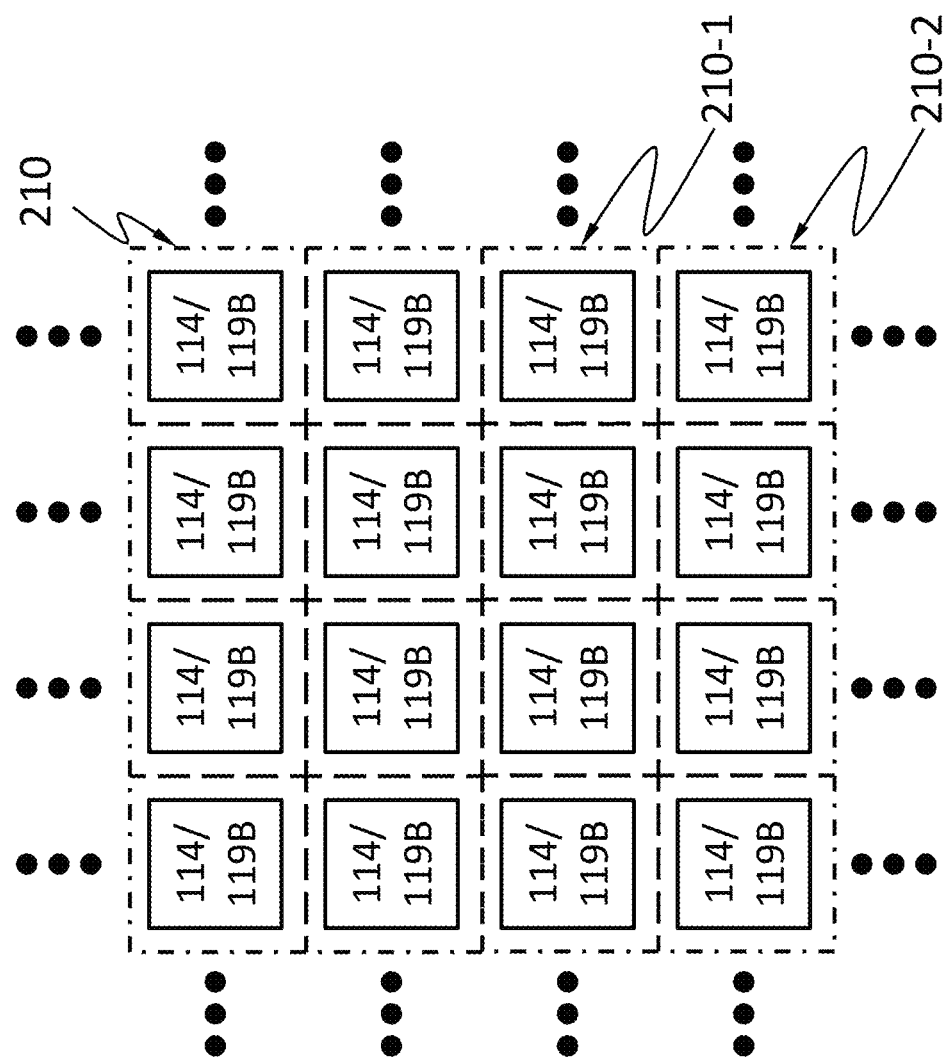

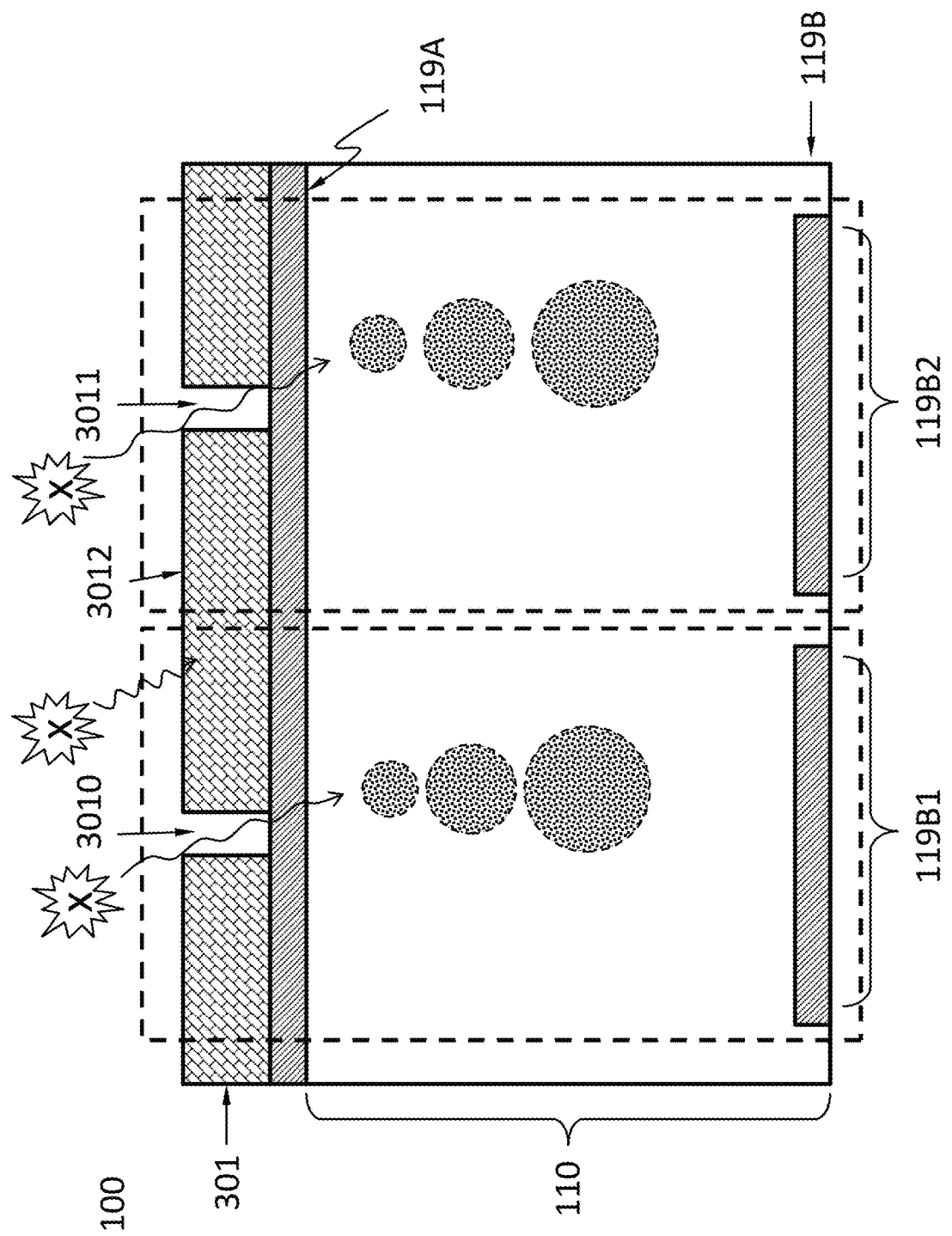

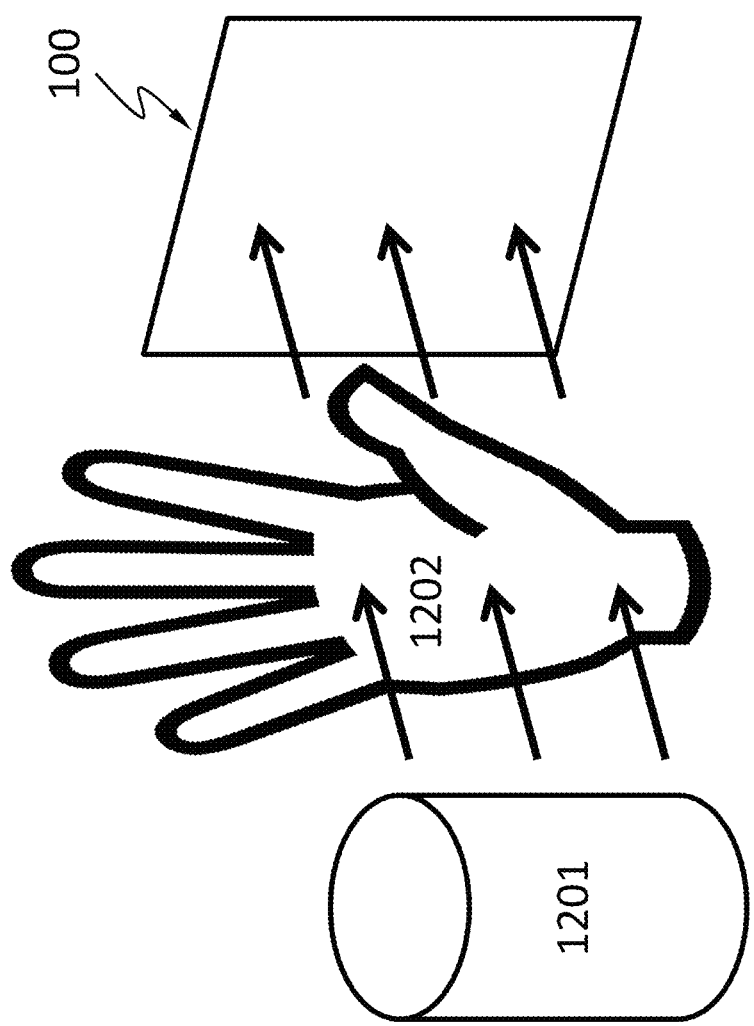

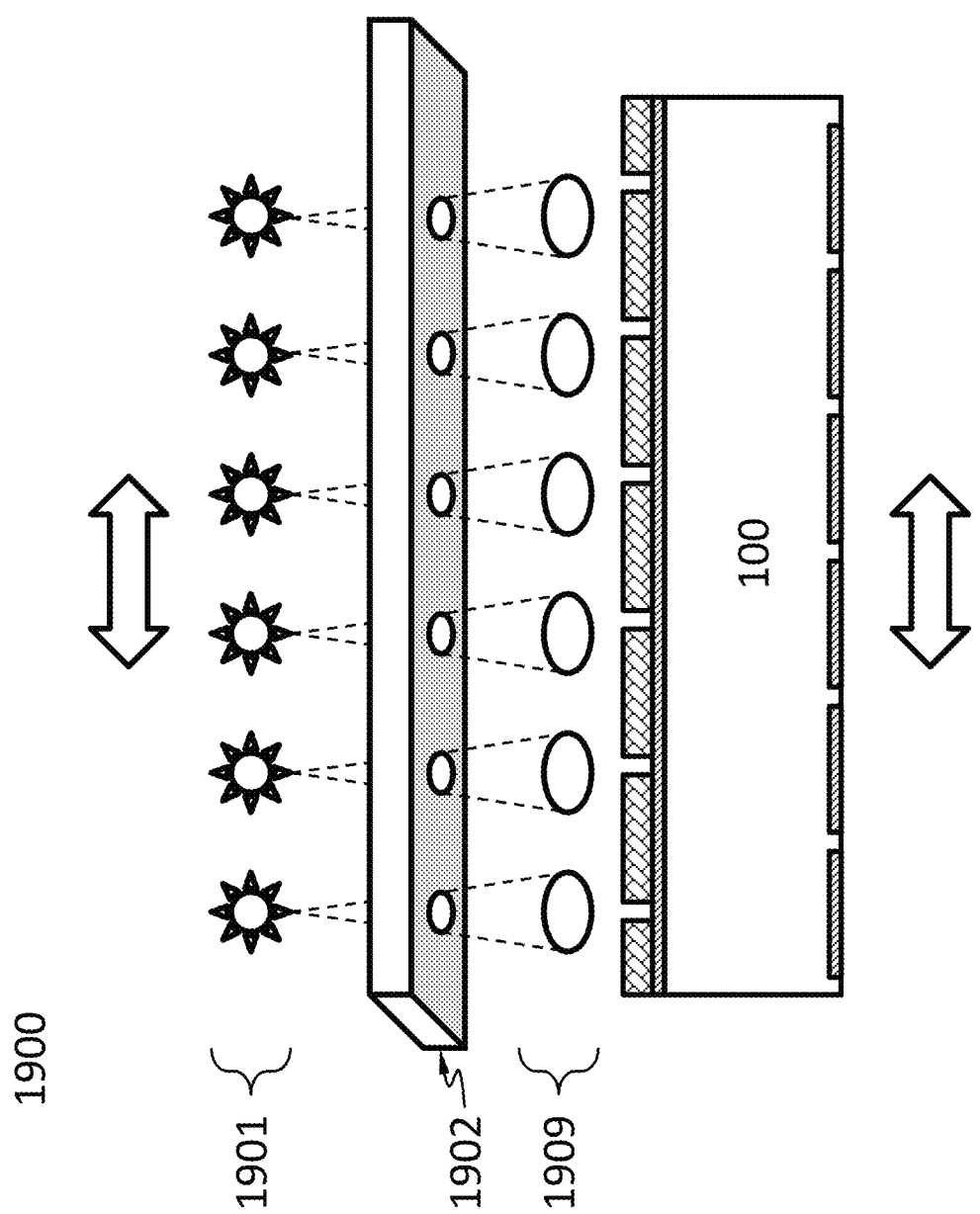

X-RAY DETECTORS OF HIGH SPATIAL RESOLUTION

TECHNICAL FIELD

The disclosure herein relates to X-ray detectors, particularly relates to X-ray detectors capable of high spatial resolution of charge carriers.

BACKGROUND

X-ray detectors may be an apparatus used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body. Another important application is elemental analysis. Elemental analysis is a process where a sample of some material is analyzed for its elemental composition.

Early X-ray detectors include photographic plates and photographic films. A photographic plate may be a glass plate with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image.

Another kind of X-ray detectors are X-ray image intensifiers. In an X-ray image intensifier, X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light.

Semiconductor X-ray detectors can directly convert X-ray into electric signals and thus offer better performance than previous generations of X-ray detectors. A semiconductor X-ray detector may include a semiconductor layer that absorbs X-ray in wavelengths of interest. When an X-ray photon is absorbed in the semiconductor layer, multiple charge carriers (e.g., electrons and holes) are generated. As used herein, the term "charge carriers," "charges" and "carriers" are used interchangeably. A semiconductor X-ray detector may have multiple pixels that can independently determine the local intensity of X-ray and X-ray photon energy. The charge carriers generated by an X-ray photon may be swept under an electric field into the pixels. If the charge carriers generated by a single X-ray photon are collected by more than one pixel ("charge sharing"), the performance of the semiconductor X-ray detector may be negatively impacted. In applications (e.g., elemental analysis) where X-ray photon energy is determined, charge sharing is especially problematic for accurate photon energy measurement, because the energy of an X-ray photon is determined by the amount of electric charges it generates. Charge sharing can also be problematic when the location of an incident X-ray photon is to be determined.

SUMMARY

The teachings disclosed herein relate to apparatus, systems and methods for X-ray detection. More particularly, the present teachings relate to apparatus, systems and methods by X-ray detectors capable of spatial resolution of charge carriers.

In one example, an apparatus suitable for detecting X-ray is disclosed. The apparatus comprises: an X-ray absorption layer and a mask; wherein the mask comprises a first window and a second window, and a portion between the first window and the second window; wherein the first and second windows are not opaque to an incident X-ray; wherein the portion is opaque to the incident X-ray; and wherein the first and second windows are arranged such that charge carriers generated in the X-ray absorption layer by an X-ray photon propagating through the first window and charge carriers generated in the X-ray absorption layer by an X-ray photon propagating through the second window do not spatially overlap.

According to an embodiment, the first window and the second window are nearest neighbors.

According to an embodiment, the apparatus further comprises a first set of one or more electrodes configured to receive a signal from the incident X-ray propagating through the first window, and a second set of one or more electrodes configured to receive a signal from the incident X-ray propagating through the second window.

According to an embodiment, receiving the signal comprises collecting charge carriers generated by the incident X-ray.

According to an embodiment, the first window or the second window or both comprises one or more through holes or one or more blind holes or a combination thereof.

According to an embodiment, the first window or the second window or both comprises one or more through slots or one or more blind slots or a combination thereof.

According to an embodiment, the first window or the second window or both comprises a material different from a material of the portion.

According to an embodiment, the mask comprises a metal.

Disclosed herein is a system comprising the apparatus described above and an X-ray source. The system is configured for performing X-ray radiography on human chest or abdomen.

Disclosed herein is a system comprising the apparatus described above and an X-ray source. The system is configured for performing X-ray radiography on human mouth.

Disclosed herein is a cargo scanning or non-intrusive inspection (NII) system, comprising the apparatus described above and an X-ray source. The cargo scanning or non-intrusive inspection (NII) system is configured for forming an image based on backscattered X-ray.

Disclosed herein is a cargo scanning or non-intrusive inspection (NII) system, comprising the apparatus described above and an X-ray source. The cargo scanning or non-intrusive inspection (NII) system is configured to form an image using X-ray transmitted through an object inspected.

Disclosed herein is a full-body scanner system comprising the apparatus described above and an X-ray source.

Disclosed herein is an X-ray computed tomography (X-ray CT) system comprising the apparatus described above and an X-ray source.

Disclosed herein is an electron microscope comprising the apparatus described above, an electron source and an electronic optical system.

Disclosed herein is a system comprising the apparatus described above. The system is configured for measuring dose of an X-ray source.

Disclosed herein is a system comprising the apparatus described above. The system is an X-ray telescope, an X-ray microscopy, an X-ray micro-CT system, or a system configured to perform mammography, industrial defect detection, microradiography, casting inspection, weld inspection, or digital subtraction angiography.

In another example, a method of using an aforementioned apparatus is disclosed. The method comprises: placing the apparatus at a plurality of positions relative to a scene; obtaining data with the apparatus at the plurality of positions; compiling an image of the scene from the data.

According to an embodiment, obtaining data comprises moving the apparatus relative to the scene.

According to an embodiment, obtaining data further comprises moving the scene relative to the apparatus.

According to an embodiment, obtaining data further comprises moving a lens relative to the scene and the apparatus.

According to an embodiment, obtaining data in the above method further comprises measuring intensity of incident X-ray propagating through each of the windows Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

FIG. 1A schematically shows a cross-sectional view of the detector, according to an embodiment.

FIG. 2A shows an exemplary top view of a portion of a semiconductor X-ray detector, according to an embodiment.

FIG. 3B schematically shows another exemplary X-ray detector capable of spatial resolution of charge carriers, according to an embodiment.

FIG. 7 schematically shows a system comprising the X-ray detector described herein, suitable for medical imaging such as chest X-ray radiography, abdominal X-ray radiography, etc., according to an embodiment.

FIG. 15 schematically shows an X-ray microscope or an X-ray micro-CT system, according to an embodiment.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

When an X-ray photon is absorbed in a semiconductor layer of an X-ray detector having an array of pixels, multiple charge carriers (e.g., electrons and holes) are generated and may be swept under an electric field towards circuitry for measuring these charge carriers. The carriers drift along the direction of the electric field and diffuse in other directions. The envelope of carrier trajectories can be roughly a conical shape. If the envelope sits on a boundary of two or more pixels of the X-ray detector, charge sharing occurs ("charge sharing" used in the present teachings means charge carriers generated from a single X-ray photon are collected by two or more pixels). Charge sharing may cause inaccurate measurement of an X-ray photon, because the energy of the X-ray photon is determined by the amount of electric charges it generates.

In the present teachings, charge sharing between neighboring pixels is limited by the X-ray detector that is capable of limiting diffusion of charge carriers, so that a single X-ray photon is only collected by a single pixel in the X-ray detector.

FIG. 1A schematically shows a semiconductor X-ray detector 100, according to an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 1B:
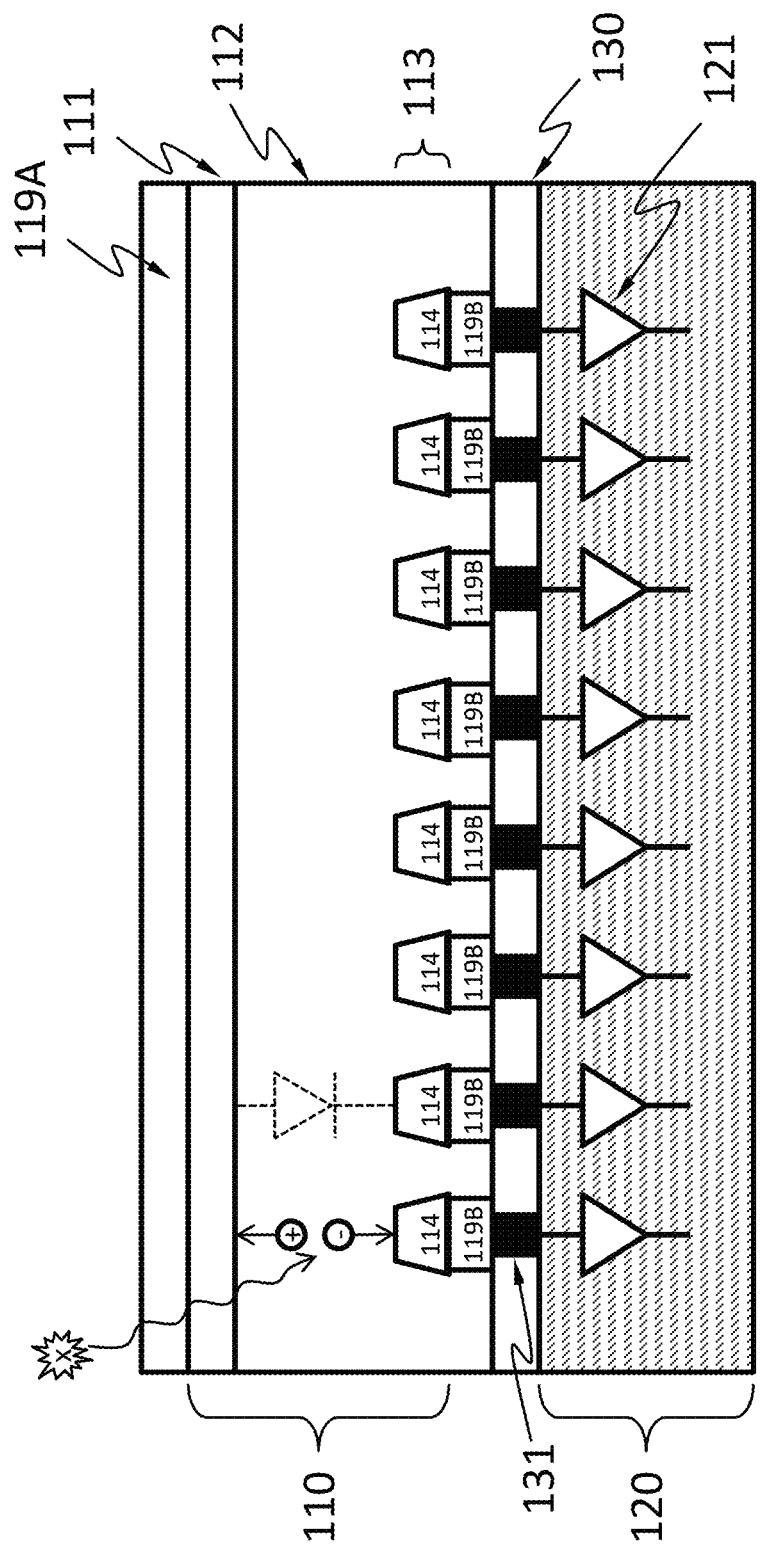
FIG. 1B schematically shows a detailed cross-sectional view of the detector, according to an embodiment.

As shown in a detailed cross-sectional view of the detector 100 in FIG. 1B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1B, each of the discrete regions 114 of the second doped region 113 forms a diode with the first doped region 111 and the optional intrinsic region 112. Namely, in the example in FIG. 1B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers generated by a single X-ray photon can be shared by two different discrete regions 114.

Figure 1C:
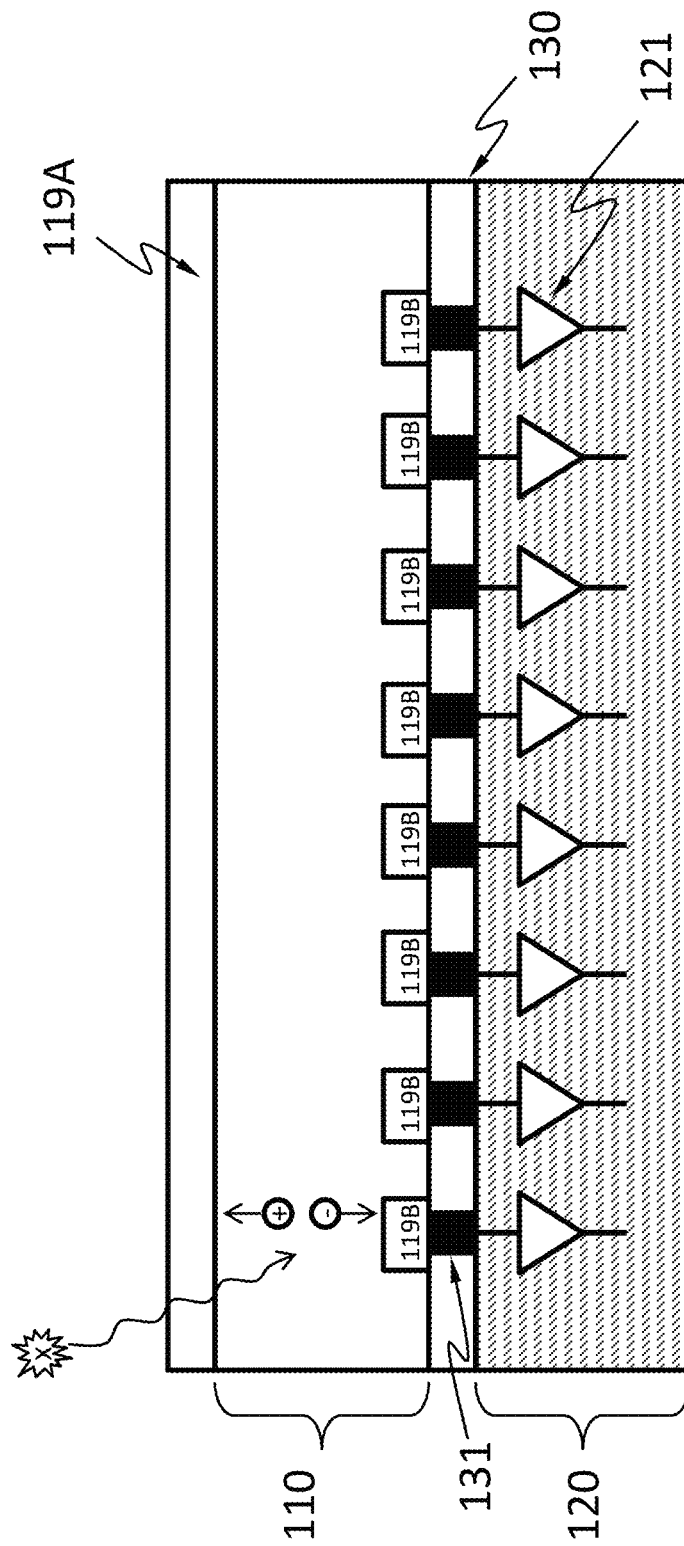
FIG. 1C schematically shows an alternative detailed cross-sectional view of the detector, according to an embodiment.

As shown in an alternative detailed cross-sectional view of the detector 100 in FIG. 1C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers generated by a single X-ray photon can be shared by two different contacts 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

FIG. 2A shows an exemplary top view of a portion of the apparatus 100 with a 4-by-4 array of discrete regions 114. Charge carriers generated by an X-ray photon incident around the footprint of one of these discrete regions 114 are not substantially shared with another of these discrete regions 114. The area 210 around a discrete region 114 in which substantially all (more than 95%, more than 98% or more than 99% of) charge carriers generated by an X-ray photon incident therein flow to the discrete region 114 is called a pixel associated with that discrete region 114. Namely, less than 5%, less than 2% or less than 1% of these charge carriers flow beyond the pixel, when the X-ray photon hits inside the pixel. The pixels may be organized in any suitable array, such as, a square array, a triangular array and a honeycomb array. The pixels may have any suitable shape, such as, circular, triangular, square, rectangular, and hexangular. The pixels may be individually addressable.

Similarly, when the 4-by-4 array in FIG. 2A indicates an array of discrete portions of the electrical contact 119B in FIG. 1B, the charge carriers generated by an X-ray photon incident around the footprint of one of these discrete portions of the electrical contact 119B are not substantially shared with another of these discrete portions of the electrical contact 119B. The area around a discrete portion of the electrical contact 119B in which substantially all (more than 95%, more than 98% or more than 99% of) charge carriers generated by an X-ray photon incident therein flow to the discrete portion of the electrical contact 119B is called a pixel associated with the discrete portion of the electrical contact 119B. Namely, less than 5%, less than 2% or less than 1% of these charge carriers flow beyond the pixel associated with the one discrete portion of the electrical contact 119B, when the X-ray photon hits inside the pixel. The pixels may be organized in any suitable array, such as, a square array, a triangular array and a honeycomb array. The pixels may have any suitable shape, such as, circular, triangular, square, rectangular, and hexangular. The pixels may be individually addressable.

As shown in FIG. 2A, two pixels 210 (e.g. 210-1 and 210-2) associated with two neighboring discrete regions 114 can be called two neighboring pixels ("neighboring pixels" used in the present teachings means pixels that are close to each other such that carriers generated from a single photon may be shared by these pixels).

Figure 2B:
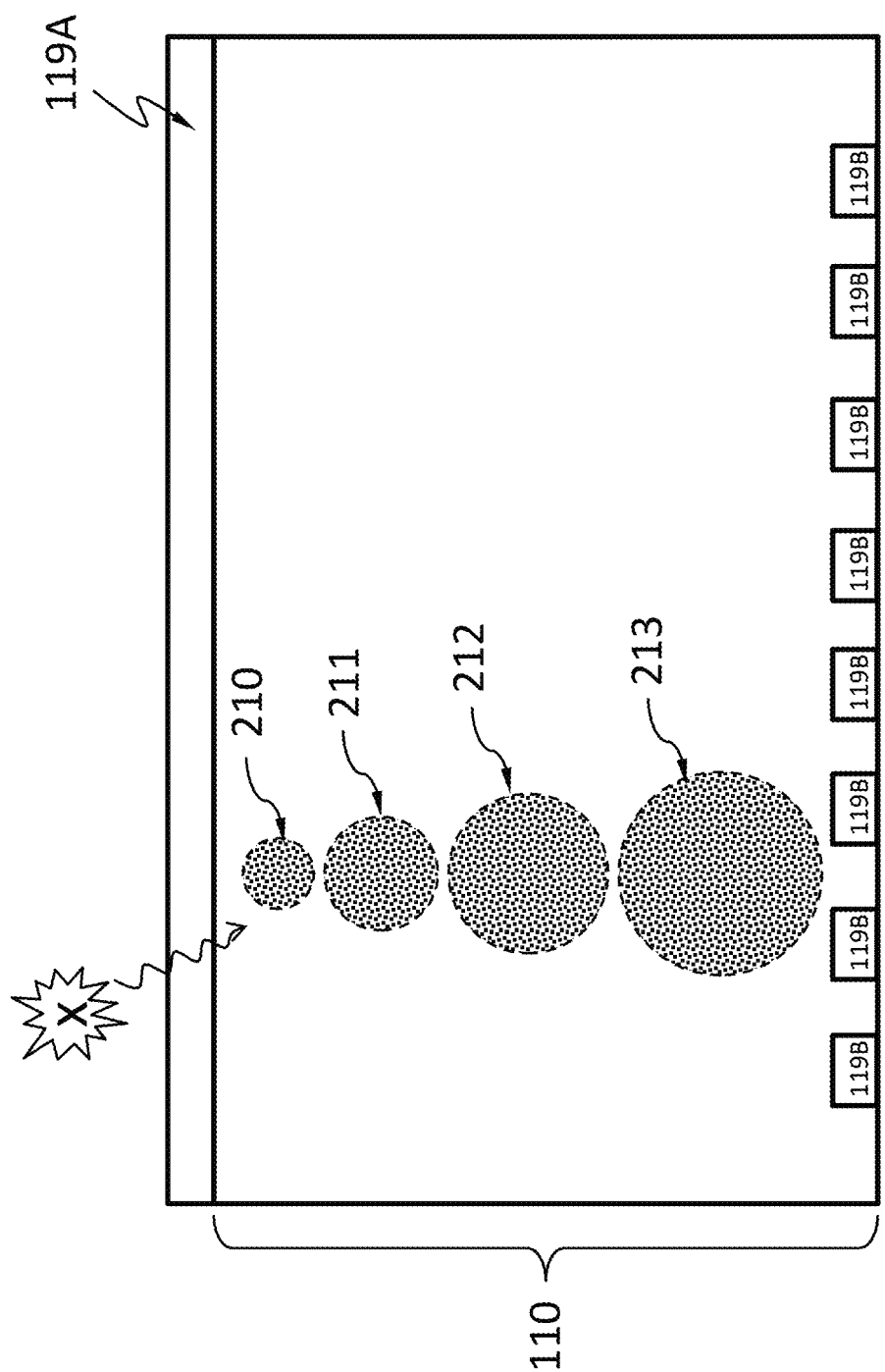
FIG. 2B schematically shows that charge carriers generated by an X-ray photon diffuse as they drift.

FIG. 2B shows an exemplary cross-sectional view of the detector with dispersing charge carriers according to an embodiment. In a semiconductor X-ray detector, charge carriers drift toward the pixels while diffuse in all directions. Regions 210, 211, 212 or 213 schematically show spaces that a group of carriers occupy as they drift toward the pixels under an electric field into the pixels.

Figure 2C:
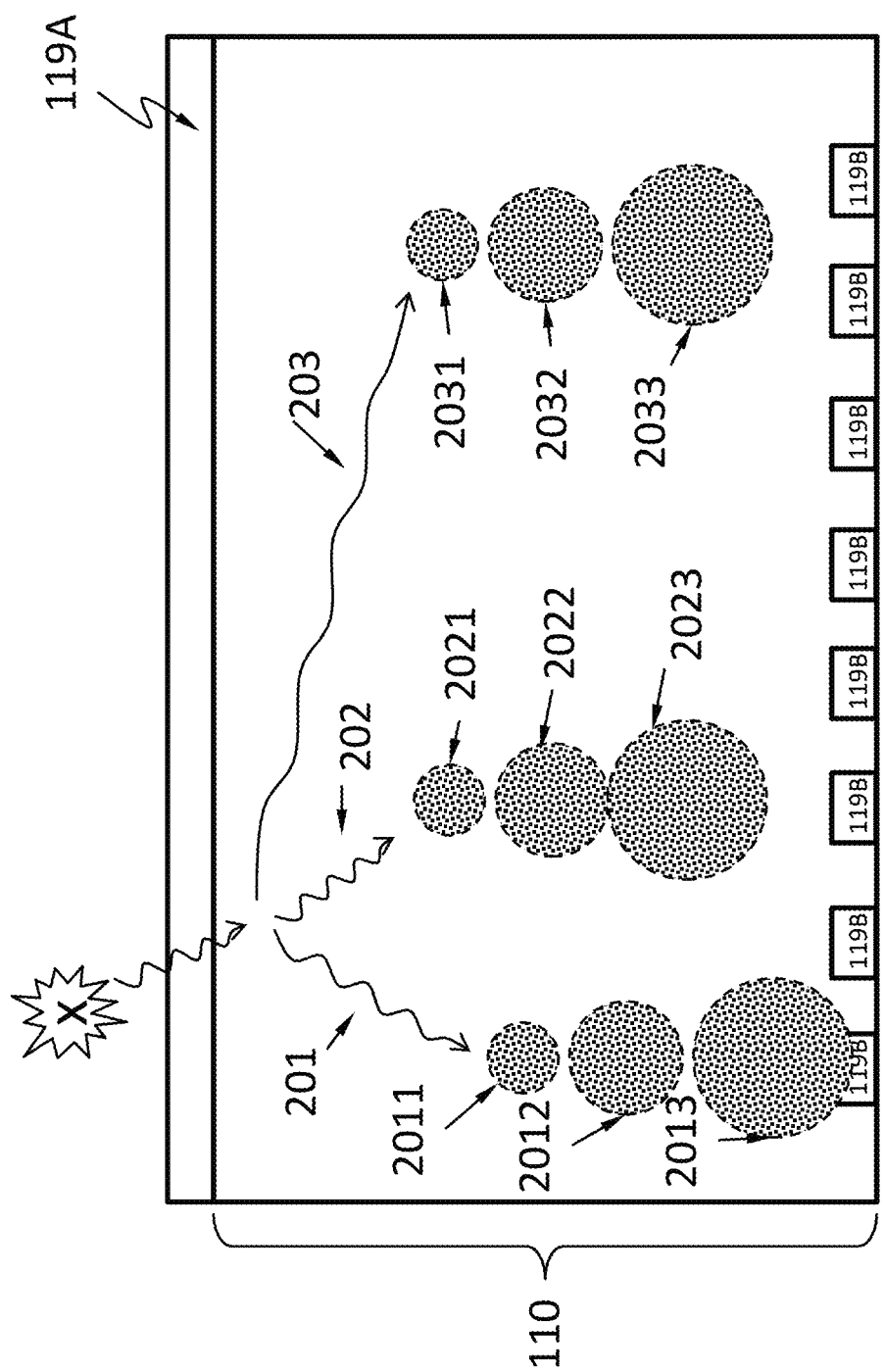
FIG. 2C schematically shows that an X-ray photon may cause X-ray fluorescence and that the fluorescent X-ray may generate charge carriers.

FIG. 2C shows that an incident X-ray photon can generate X-ray fluorescence. Namely, secondary X-ray photons such as 201, 202, and 203 may be generated and they can generate additional charge carriers at locations relatively far away from where the incident photon hits.

The incident X-ray photon and the secondary X-ray photons can be absorbed and cause multiple charge carriers to be generated. The charge carriers may move in various directions, e.g. drift along the direction of an electric field and diffuse in other directions. In FIG. 2C, each circle, e.g. 2011, 2012, 2013, 2021, 2022, 2023, 2031, 2032 and 2033, represents the footprint of a region of charge carriers generated by a photon occupy at a point of time.

FIG. 2C also illustrates a mechanism of charge sharing. A region the charge carriers occupy may be inside a pixel, or on a boundary of neighboring pixels (e.g. region 2033).

As discussed above, when a region that the charge carriers occupy is over a boundary of two or more neighboring pixels, charge sharing occurs, which may cause issue for energy measurement. In an embodiment, the electronic system 121 in an X-ray detector can still accurately measure the energy of an X-ray photon even if a charge sharing occurs to the carriers generated by the X-ray photon.

According to an embodiment, two neighboring pixels do not have to share a boundary, but can be close to each other such that carriers generated from a single photon may be shared by the two pixels. That is, charge sharing may occur on neighboring pixels, even if there is not a boundary shared by the neighboring pixels.

If the size of a pixel is too small, e.g. smaller than a region the charge carriers occupy when the charge carriers reach the pixel, charge sharing can happen all the time. On the other hand, if the size of a pixel is too large, it is very likely for multiple photons to hit the pixel at the same time, which can generate difficulty for accurate X-ray detection and image generation.

Figure 3A:
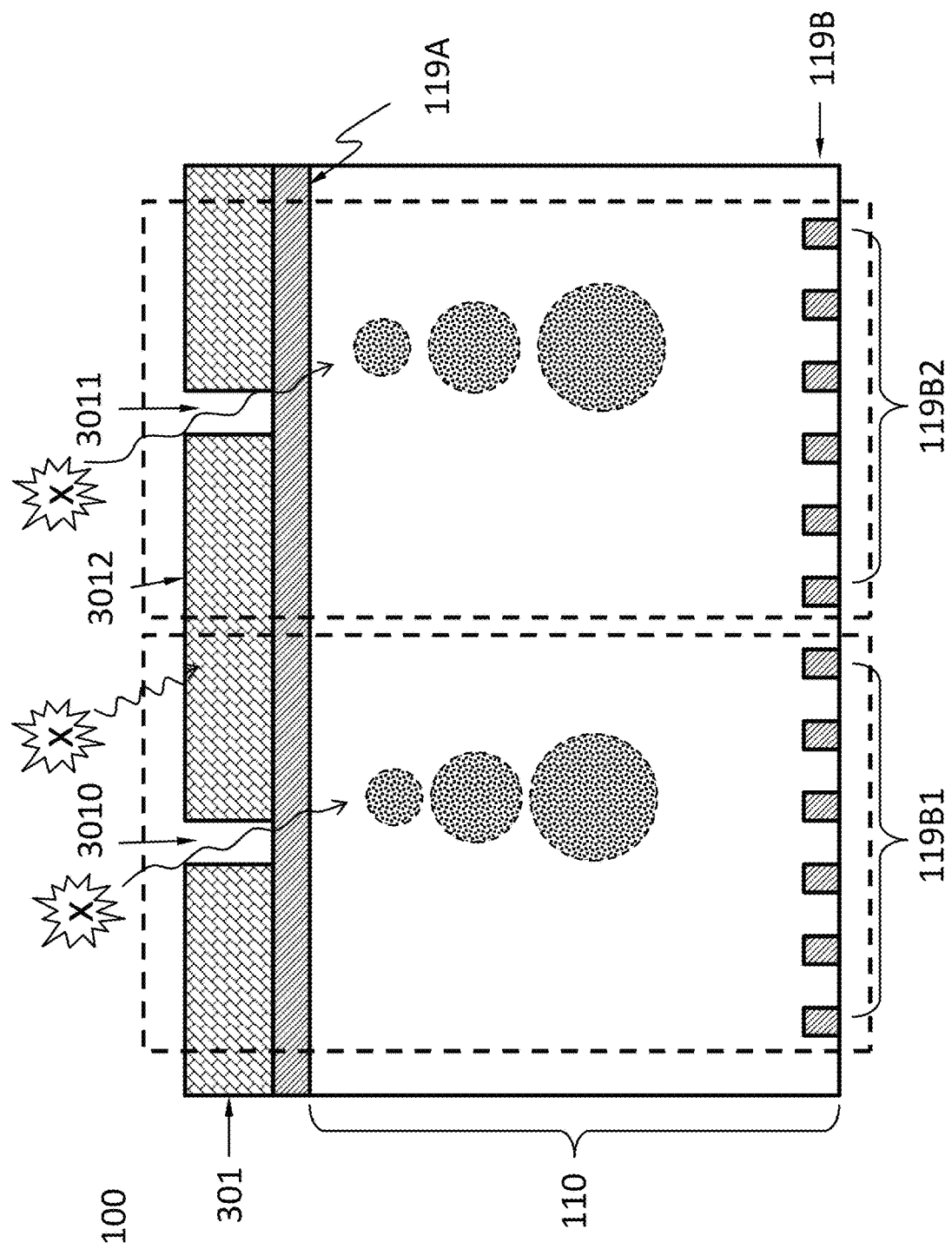
FIG. 3A schematically shows an exemplary X-ray detector capable of spatial resolution of charge carriers, according to an embodiment.

FIG. 3A schematically shows a semiconductor X-ray detector 100, according to an embodiment. The semiconductor X-ray detector 100 can include an X-ray absorption layer 110 described above and a mask 301. The mask 301 may include multiple windows such as a window 3010 and a window 3011, and a portion 3012 separating the windows from one another. The window 3010 is the nearest neighbor of window 3011. As used herein, a window A being the nearest neighbor of a window B means that no other window is closer to window B than window A is. The distance between two windows may be the center-to-center distance. As used herein, a center of a window is defined as the center of the three dimensional space within the window.

The windows are not opaque to an incident X-ray. For example, the windows may have an X-ray transmissivity of at least 80% or at least 90%.

The portion that separates the windows is essentially opaque to the incident X-ray. For example, the portion may have an X-ray transmissivity of at most 20% or at most 10%.

The windows 3010 and 3011 are arranged such that charge carriers generated in the X-ray absorption layer 110 by an X-ray photon propagating through the window 3010 and charge carriers generated in the X-ray absorption layer 110 by an X-ray photon propagating through the window 3011 do not spatially overlap.

Multiple electrical contacts 119B may be configured to receive a signal (e.g., detect charge carriers generated) from an X-ray photon propagating through a single window, as schematically shown in FIG. 3A. In one example, a first set 119B1 among the electrical contacts 119B is configured to receive a signal from the incident X-ray propagating through the window 3010; and a second set 11962 among the electrical contacts 119B is configured to receive a signal from the incident X-ray propagating through the window 3011.

According to an embodiment, receiving the signal may include collecting charge carriers generated by the incident X-ray. When multiple electrical contacts are used to receive a signal from a single photon transmitting through a window, the signals received may be combined to arrive at the total signal from the single photon. For example, the amounts of charge carriers received by the set 119B1 may be summed to arrive at the total amount of charge carriers generated by a photon through the window 3010. Because the windows 3010 and 3011 are arranged such that charge carriers generated through each window do not have spatial overlap, all the signals received by the set 119B1 must be from a photon incident on the detector at the window 3010 and all the signals received by the set 11962 must be from a photon incident on the detector at the window 3011.

Figure 3C:
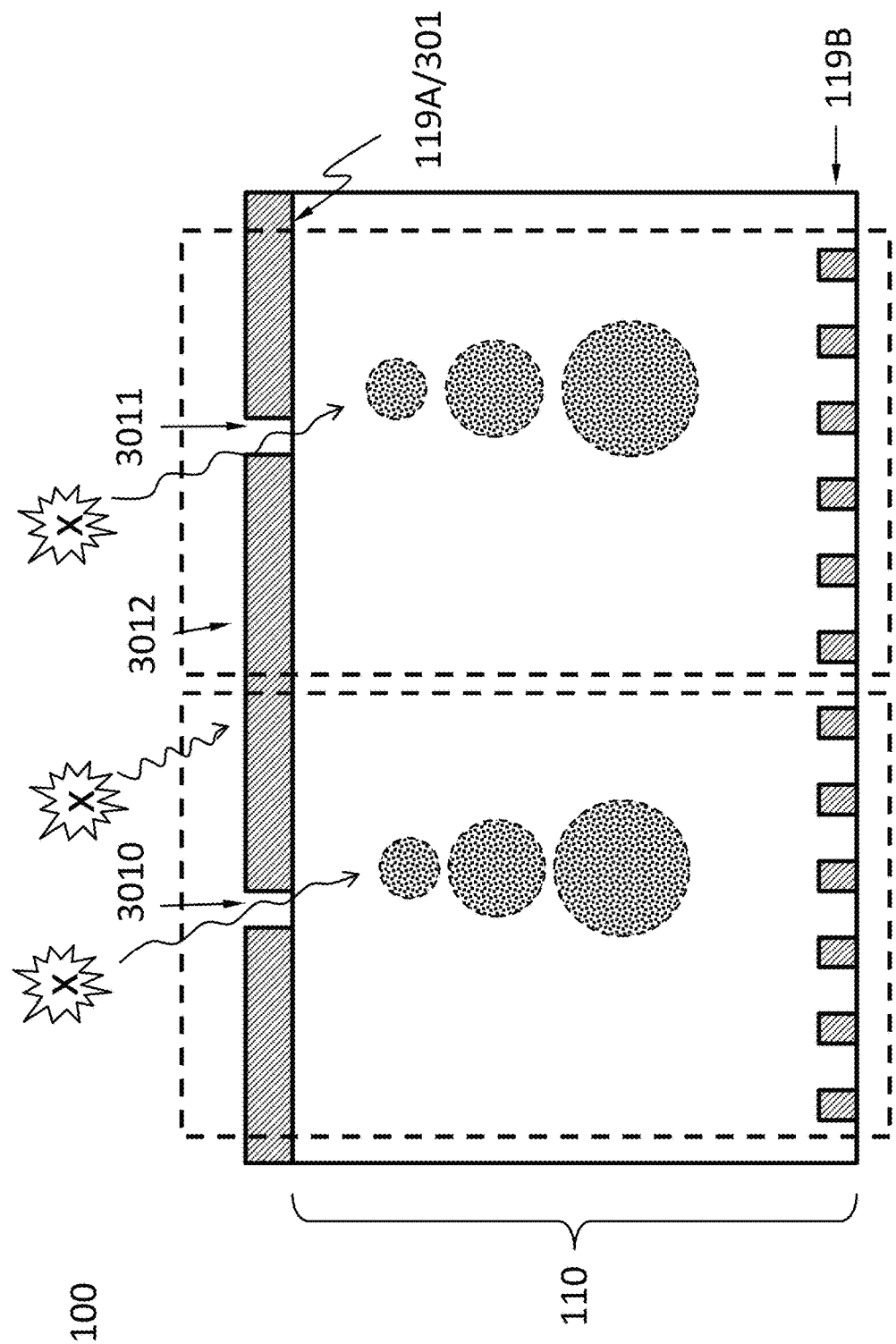
FIG. 3C schematically another exemplary X-ray detector capable of spatial resolution of charge carriers, according to an embodiment.

It is conceivable that various arrangements of the electrical contacts 119B may be provided for the X-ray detector 100. For example, as schematically shown in FIG. 3B, a single electrical contact 119B1 and 11962 are configured to respectively receive essentially all signal from an X-ray photon transmitted through the window 3010 and the window 3011. The single electrical contact 119B1 and 11962 can be almost as large as the spacing between the windows 3010 and 3011 but are not necessarily that large. FIG. 3C schematically shows that the mask 301 may be part of the electrical contacts 119A.

Figure 4A:
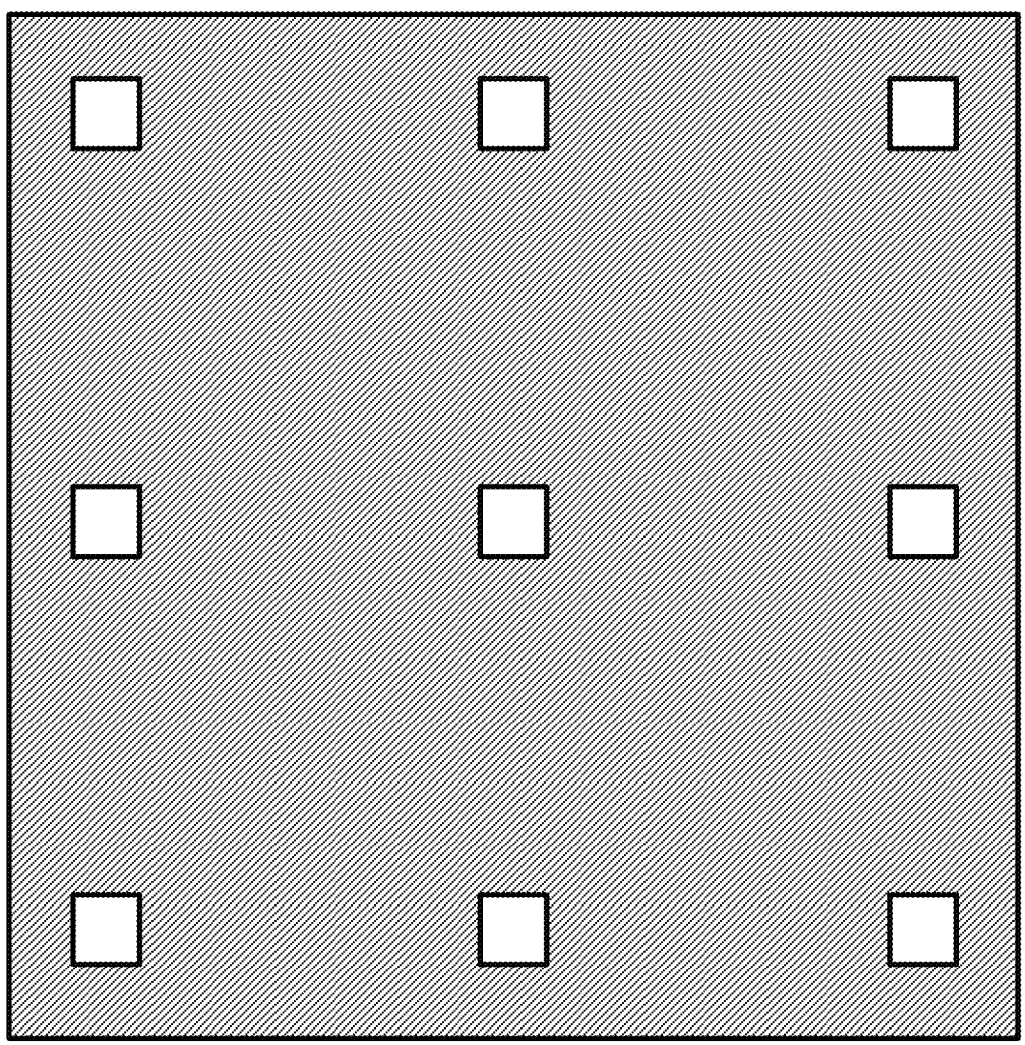
FIG. 4A schematically shows an exemplary top view of an X-ray detector capable of spatial resolution of charge carriers, according to an embodiment.
Figure 4B:
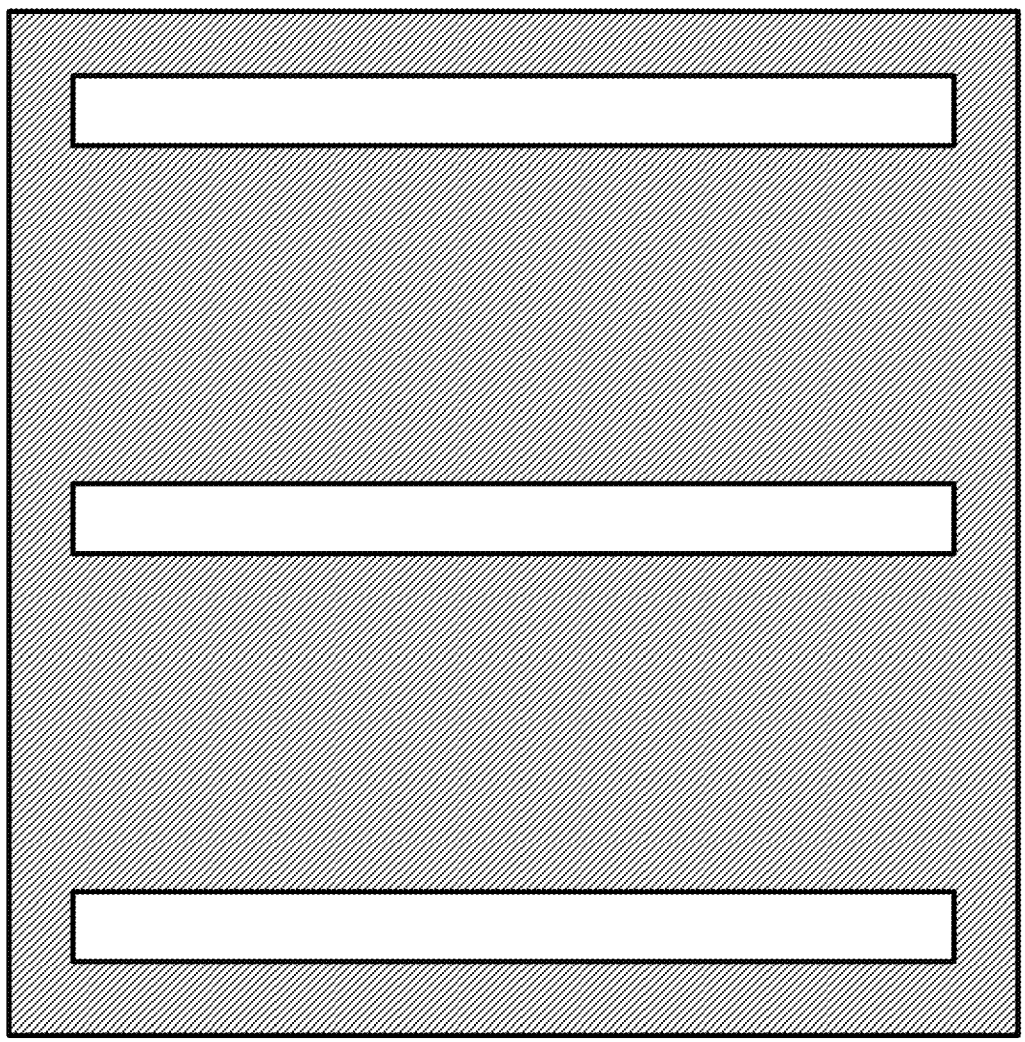
FIG. 4B schematically shows another exemplary top view of an X-ray detector capable of spatial resolution of charge carriers, according to an embodiment.

The windows in the mask 301 may have any suitable shapes and arrangements. For example, the windows may have regular shapes or irregular shapes, such as round, rectangular, square, polygonal, slot or other irregular shapes. For example, the windows may be arranged in a two-dimensional array with equal or unequal window-to-window distance. One such example is schematically shown in FIG. 4A. The windows may be arranged in a tandem sequence, i.e., a one-dimensional array with equal or unequal window-to-window distance. One such example is schematically shown in FIG. 4B. The two-dimensional array arrangement of the windows may be used where spatial resolution in both directions of a scene is needed. The one-dimensional array arrangement of the windows may be used where spatial resolution in one direction of a scene is needed.

The mask 301 may be a metal (e.g., gold, platinum) film or other suitable materials that are efficient in blocking X-ray.

According to an embodiment, the windows may be blind holes, i.e. the materials in the space occupied by the windows can be partially removed by a suitable method such as etching, reaming, drilling, or milling, without breaking through to the other side of the mask.

According to an embodiment, the windows may be through holes, i.e. the materials in the space occupied by the windows can be completely removed by a suitable method such as etching, reaming, drilling, or milling, such that the windows are open to the both sides of the mask. The windows of one mask may be a mixture of blind holes and through holes. The windows may be patterned using a suitable technique such as a stencil or lithography.

The windows may be left unfilled or partially or completely filled with a material different from the rest of the mask.

The windows may be filled with a different material from that of the mask after being formed into either a blind hole or a through hole, and as such, the window and the portion are of different materials. For example, the filling material for the window may be aluminum.

Figure 5:
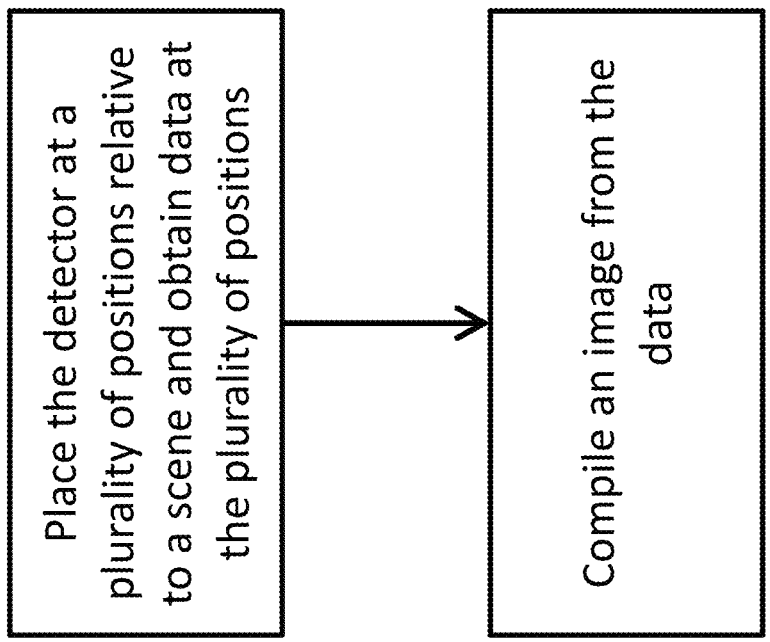
FIG. 5 schematically shows an exemplary method of using an X-ray detector capable of spatial resolution of charge carriers, according to an embodiment.

FIG. 5 schematically shows a method of using the detector disclosed above. The method may include: placing the detector at a plurality of positions relative to a scene; obtaining data with the detector at the plurality of positions; compiling an image of the scene from the data.

Figure 6A:
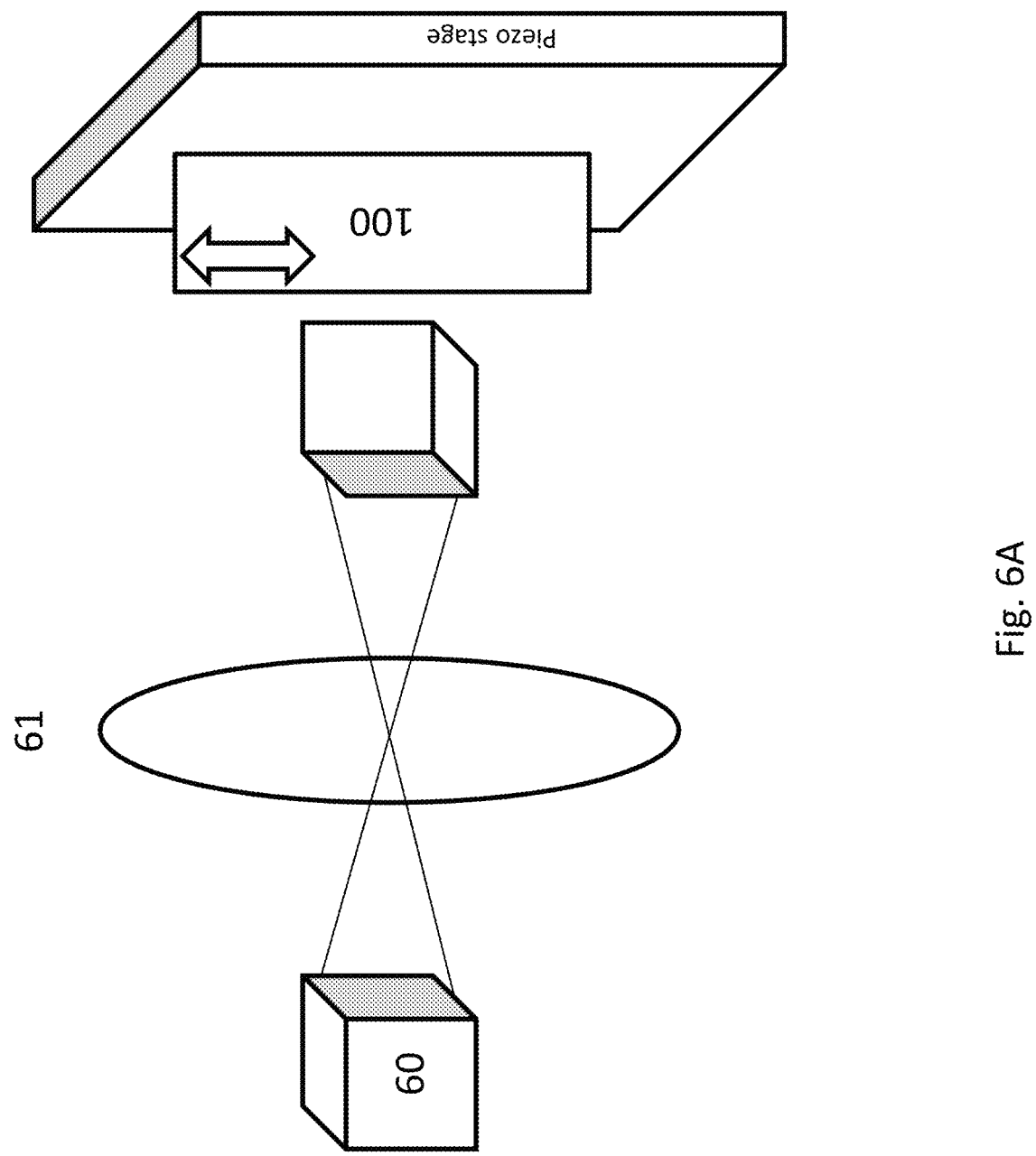
FIG. 6A schematically shows an exemplary method of using an X-ray detector capable of spatial resolution of charge carriers by moving the X-ray detector relative to the scene, according to an embodiment.

As shown in FIG. 6A, obtaining data in the above method may include moving the detector 100 relative to the scene 60.

Figure 6B:
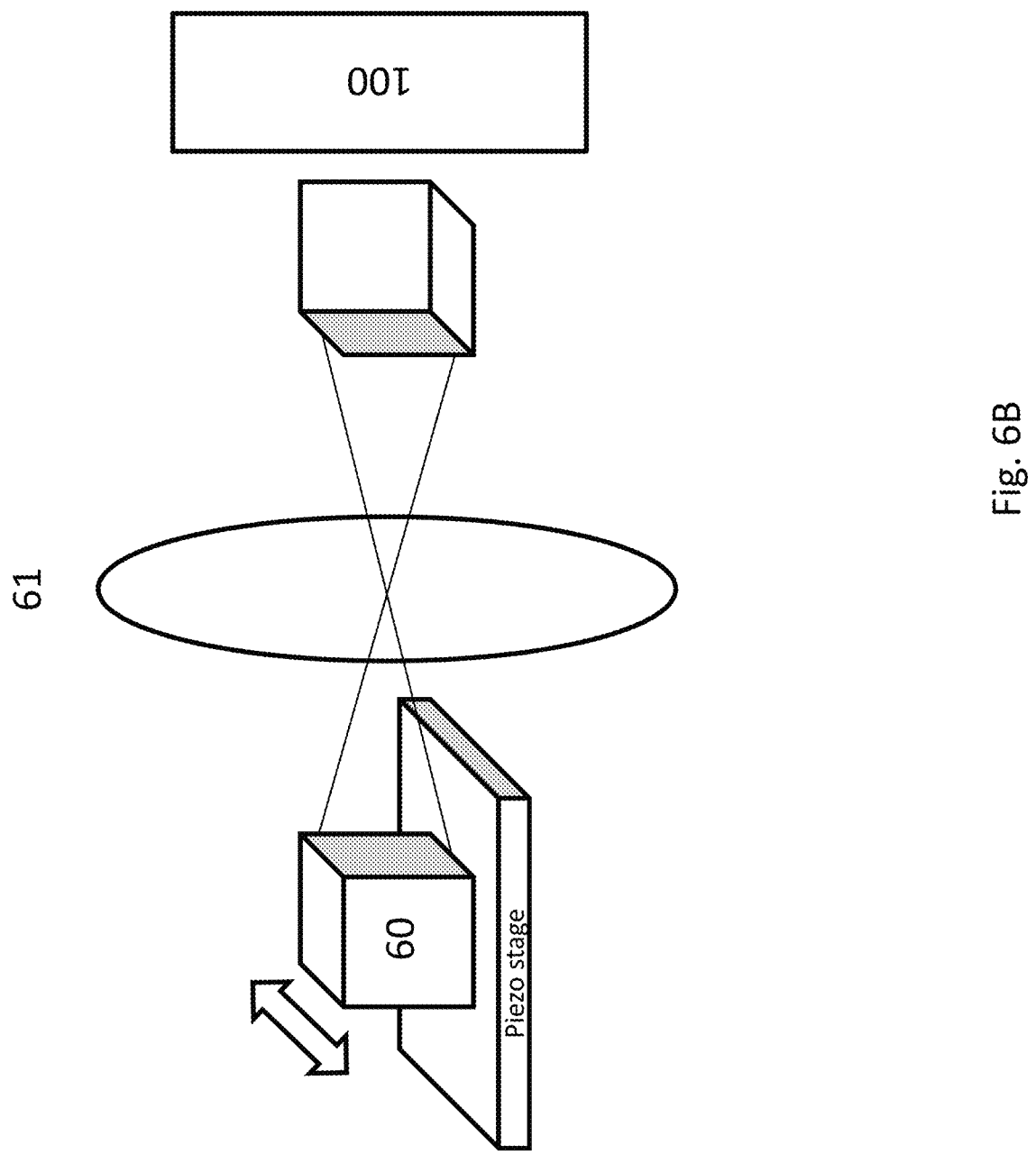
FIG. 6B schematically shows another exemplary method of using an X-ray detector capable of spatial resolution of charge carriers by moving the scene relative to the X-ray detector, according to an embodiment.

As shown in FIG. 6B, obtaining data in the above method may include moving the scene 60 relative to the detector 100.

Figure 6C:
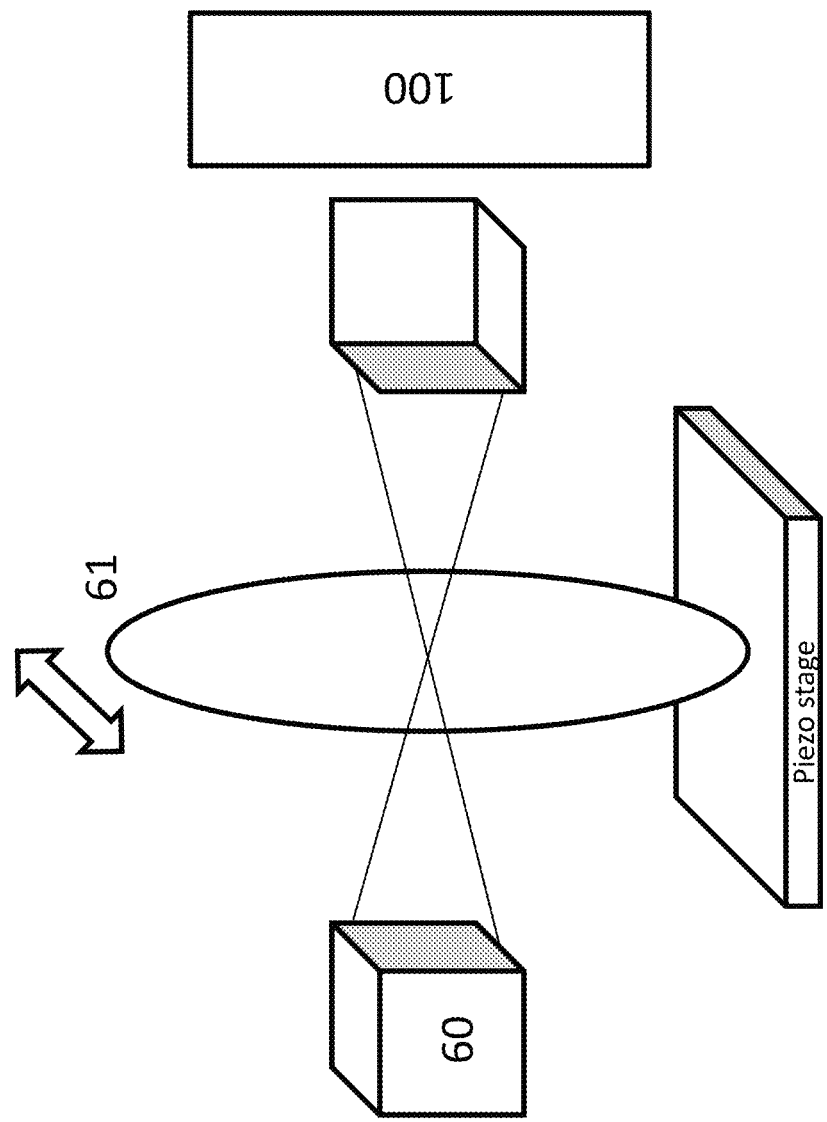
FIG. 6C schematically shows another exemplary method of using an X-ray detector capable of spatial resolution of charge carriers by moving the lens, according to an embodiment.

As shown in FIG. 6C, an optical system such as a lens 61 is used to form the scene 60, and obtaining data in the above method may include moving the lens 61 relative to the detector 100 and the scene 60.

The image may be formed by measuring intensity of incident X-ray propagating through each of the windows.

Various exemplary embodiments of applications of the above X-ray detector are provided below.

FIG. 7 schematically shows a system comprising the semiconductor X-ray detector 100 described herein. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the semiconductor X-ray detector 100. The semiconductor X-ray detector 100 forms an image by detecting the intensity distribution of the X-ray.

Figure 8:
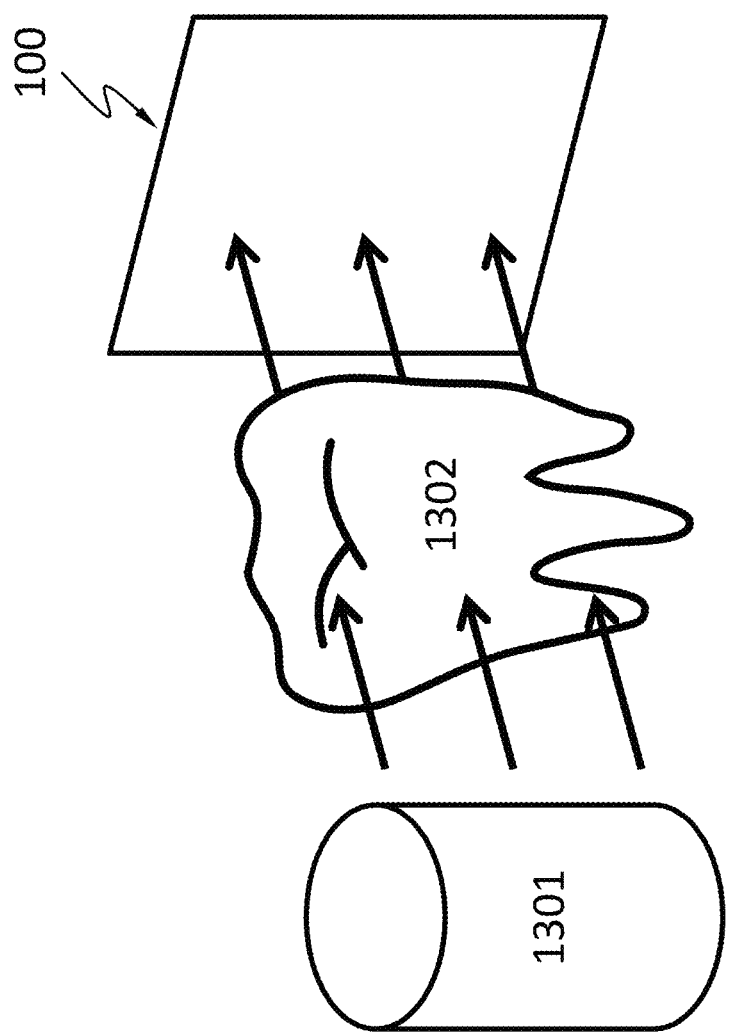
FIG. 8 schematically shows a system comprising the X-ray detector described herein suitable for dental X-ray radiography, according to an embodiment.

FIG. 8 schematically shows a system comprising the semiconductor X-ray detector 100 described herein. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the semiconductor X-ray detector 100. The semiconductor X-ray detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 9:
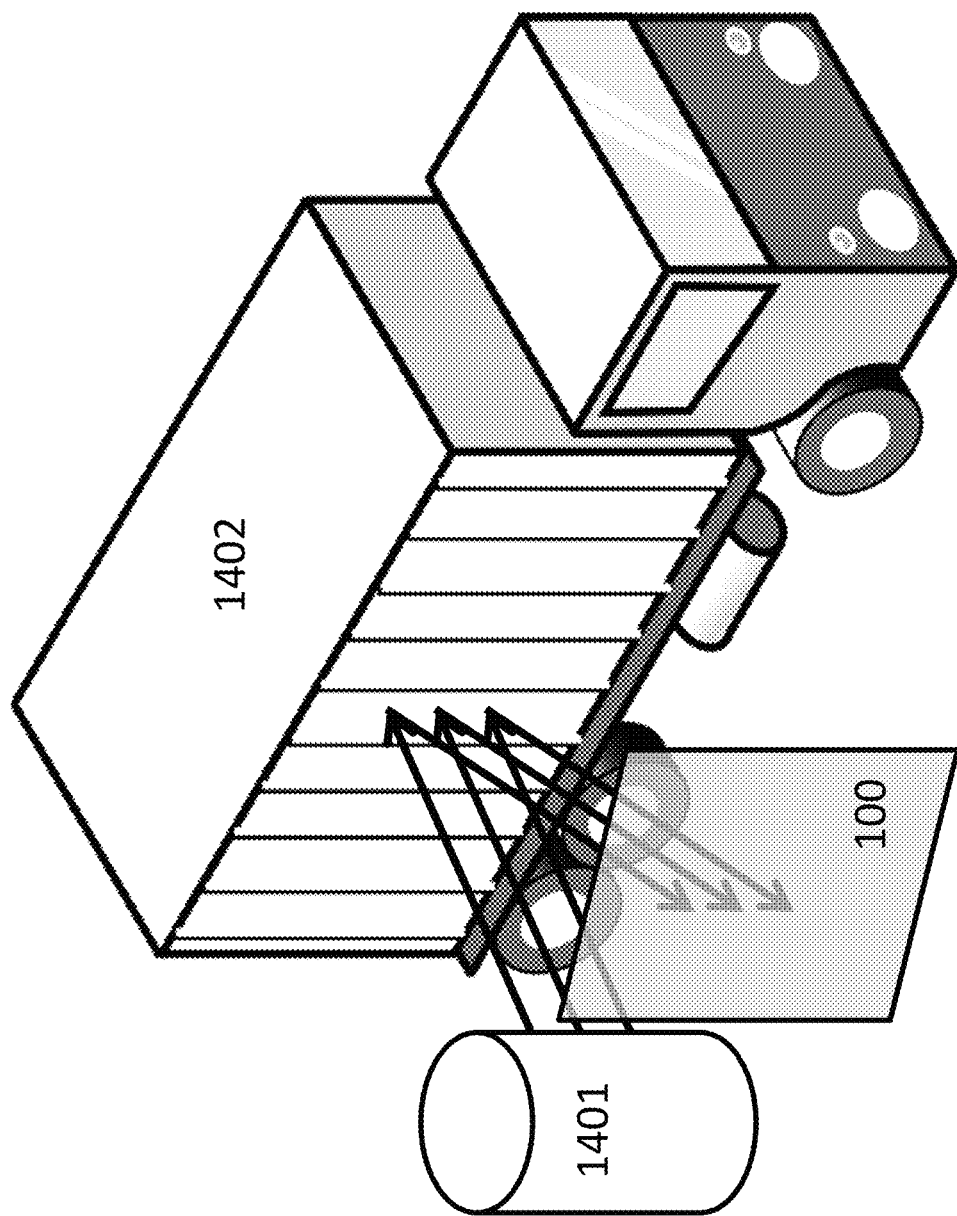
FIG. 9 schematically shows a cargo scanning or non-intrusive inspection (NII) system comprising the X-ray detector described herein, according to an embodiment.

FIG. 9 schematically shows a cargo scanning or non-intrusive inspection (NII) system comprising the semiconductor X-ray detector 100 described herein. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the semiconductor X-ray detector 100. Different internal structures of the object 1402 may backscatter X-ray differently. The semiconductor X-ray detector 100 forms an image by detecting the intensity distribution of the backscattered X-ray and/or energies of the backscattered X-ray photons.

Figure 10:
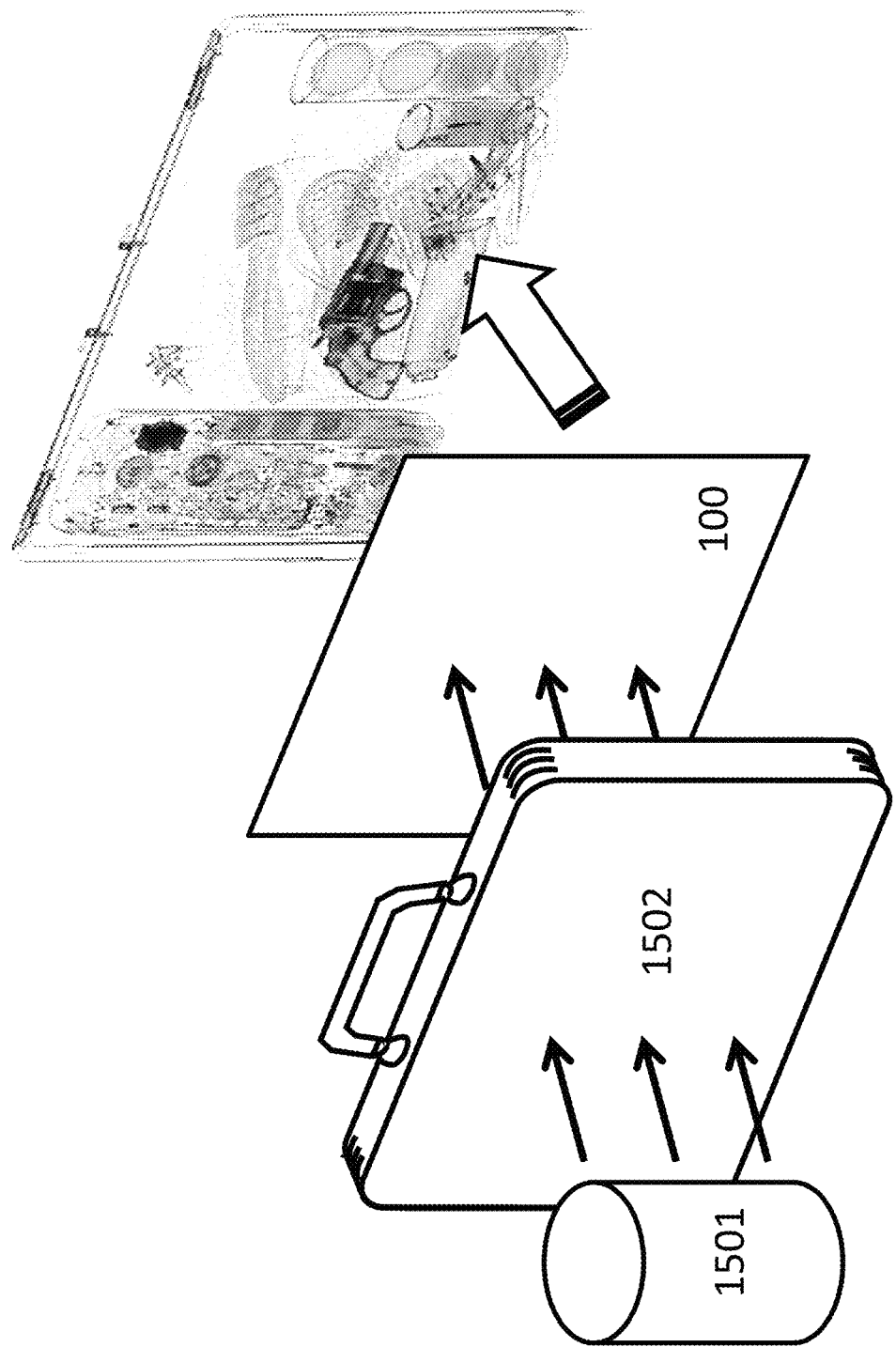
FIG. 10 schematically shows another cargo scanning or non-intrusive inspection (NII) system comprising the X-ray detector described herein, according to an embodiment.

FIG. 10 schematically shows another cargo scanning or non-intrusive inspection (NII) system comprising the semiconductor X-ray detector 100 described herein. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the semiconductor X-ray detector 100. The semiconductor X-ray detector 100 forms an image by detecting the intensity distribution of the transmitted X-ray. The system may reveal contents of luggage and identify items forbidden on public transportation, such as firearms, narcotics, edged weapons, flammables.

Figure 11:
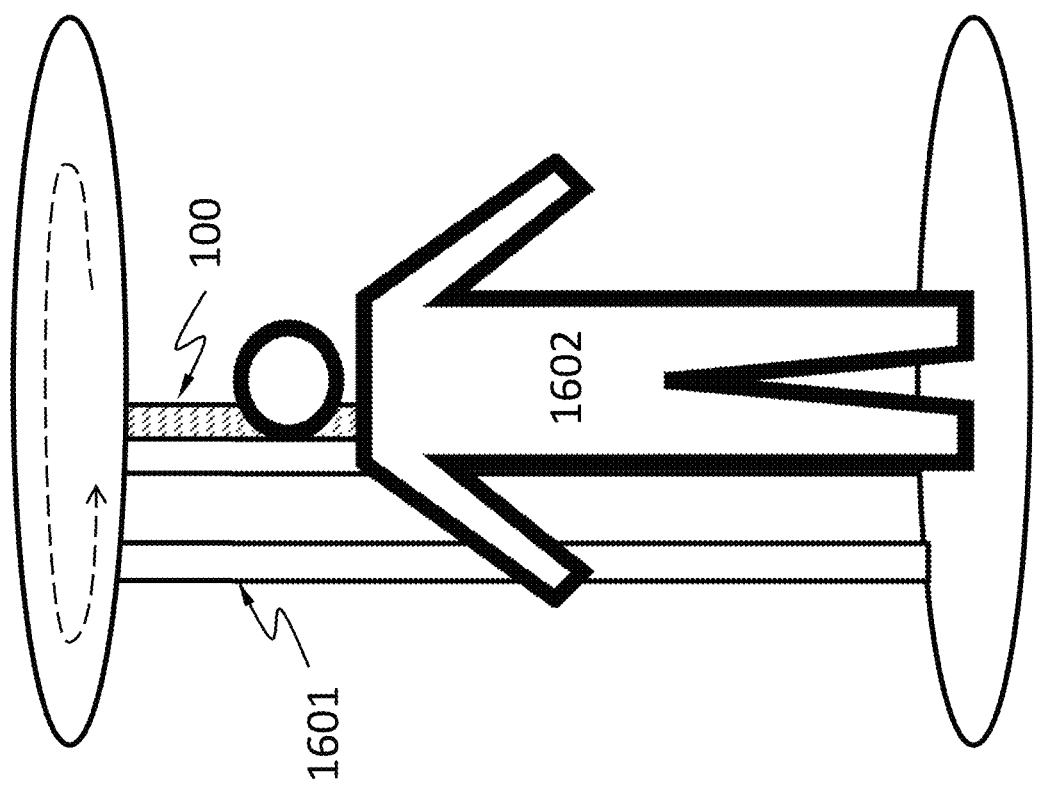
FIG. 11 schematically shows a full-body scanner system comprising the X-ray detector described herein, according to an embodiment.

FIG. 11 schematically shows a full-body scanner system comprising the semiconductor X-ray detector 100 described herein. The full-body scanner system may detect objects on a person's body for security screening purposes, without physically removing clothes or making physical contact. The full-body scanner system may be able to detect non-metal objects. The full-body scanner system comprises an X-ray source 1601. X-ray emitted from the X-ray source 1601 may backscatter from a human 1602 being screened and objects thereon, and be projected to the semiconductor X-ray detector 100. The objects and the human body may backscatter X-ray differently. The semiconductor X-ray detector 100 forms an image by detecting the intensity distribution of the backscattered X-ray. The semiconductor X-ray detector 100 and the X-ray source 1601 may be configured to scan the human in a linear or rotational direction.

Figure 12:
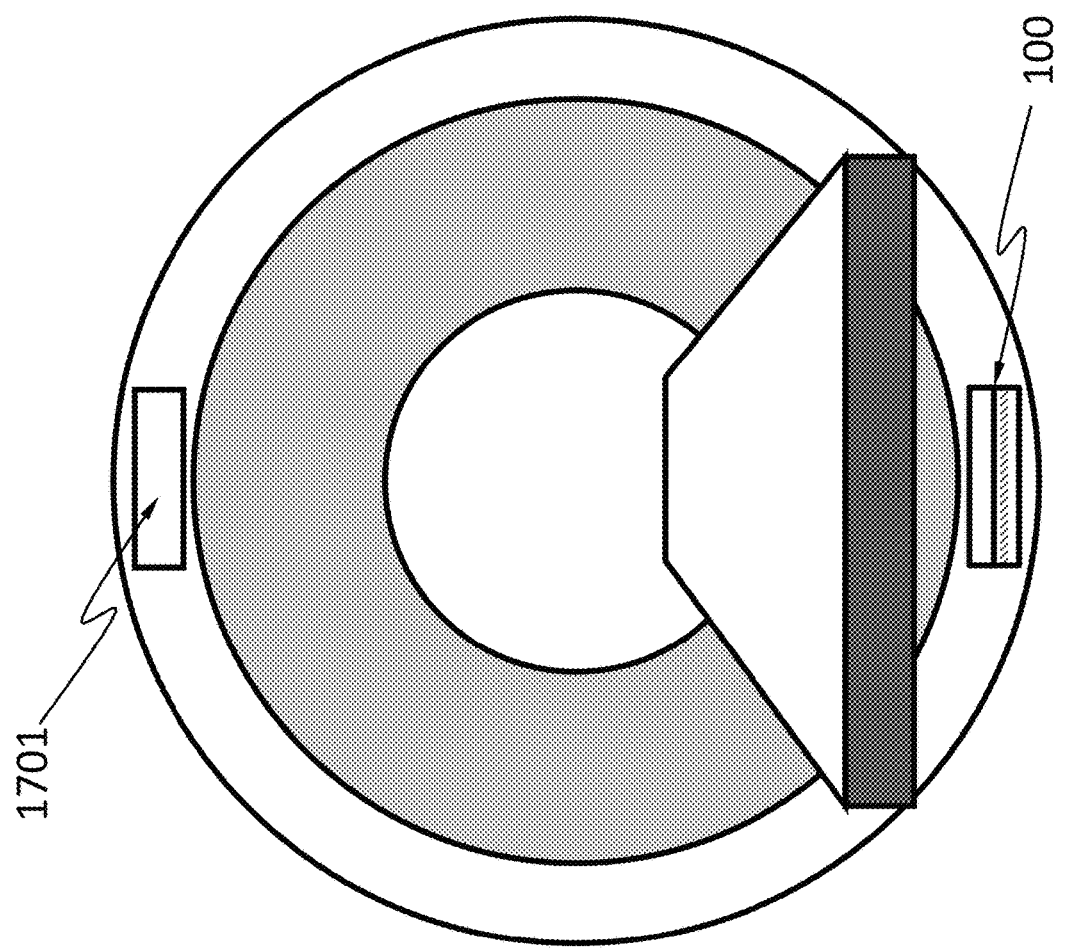
FIG. 12 schematically shows an X-ray computed tomography (X-ray CT) system comprising an X-ray detector described herein, according to an embodiment.

FIG. 12 schematically shows an X-ray computed tomography (X-ray CT) system comprising the semiconductor X-ray detector 100 described herein. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 100 described herein and an X-ray source 1701. The semiconductor X-ray detector 100 and the X-ray source 1701 may be configured to rotate synchronously along one or more circular or spiral paths.

Figure 13:
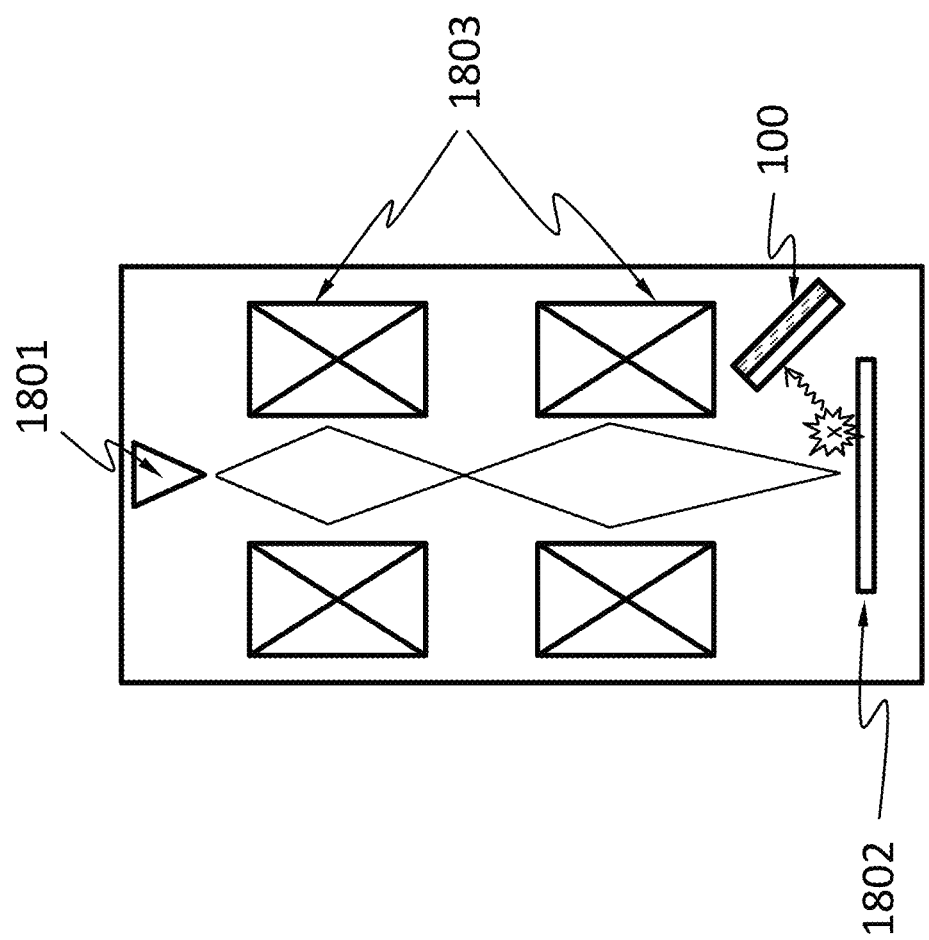
FIG. 13 schematically shows an electron microscope comprising the X-ray detector described herein, according to an embodiment.

FIG. 13 schematically shows an electron microscope comprising the semiconductor X-ray detector 100 described herein. The electron microscope comprises an electron source 1801 (also called an electron gun) that is configured to emit electrons. The electron source 1801 may have various emission mechanisms such as thermionic, photo-cathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the semiconductor X-ray detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the semiconductor X-ray detector 100.

Figure 14:
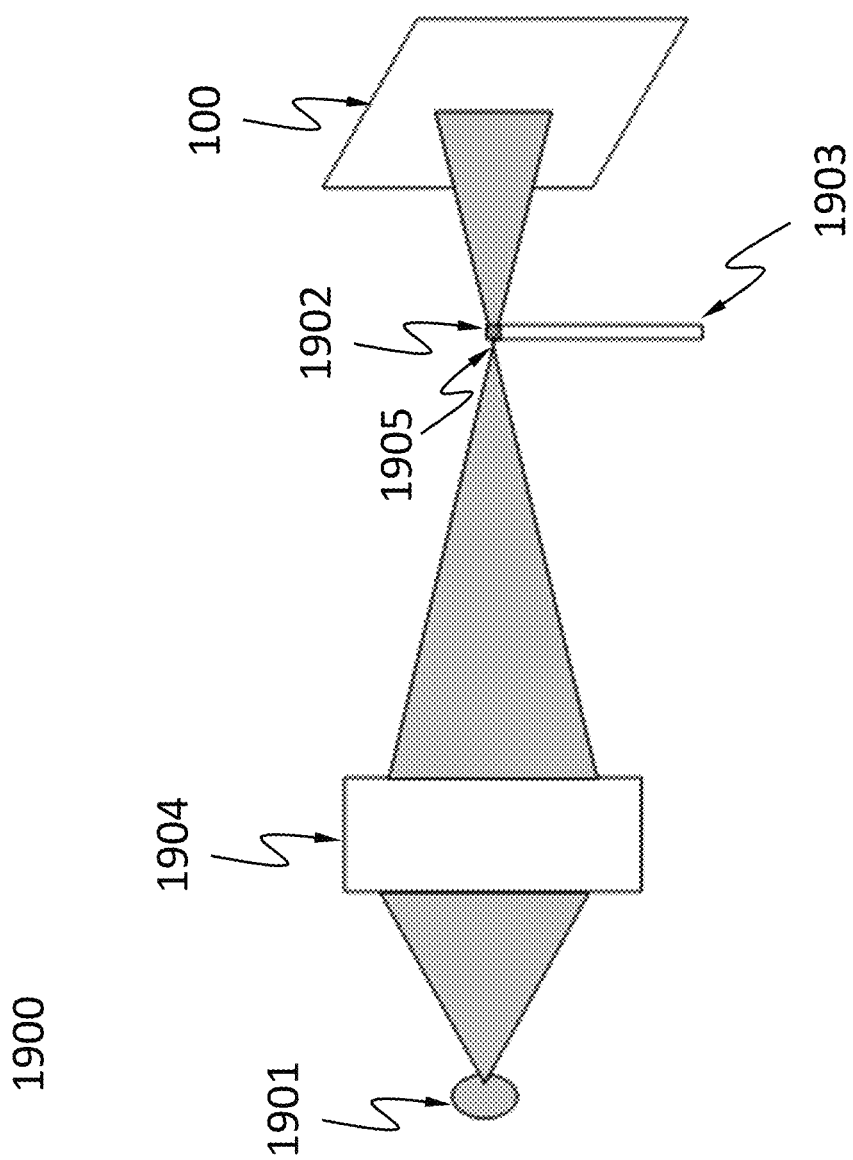
FIG. 14 schematically shows an X-ray microscope or an X-ray micro-CT system, according to an embodiment.

FIG. 14 schematically shows an X-ray microscope or an X-ray micro-CT system 1900 comprising the semiconductor X-ray detector 100 described herein, according to an embodiment. The X-ray microscope 1900 may include an X-ray source 1901, a focusing optics 1904, and the detector 100 for detecting the resulting X-ray image of the sample 1902.

The X-ray source 1901 may be a microfocus X-ray source with a size of 5 to 20 μm. The focusing optics 1904 may help to focus the X-ray irradiated from the X-ray source 1901 into a focal point 1905, which forms a tiny virtual source. The focal point 1905 may have a size of 1 to 100 nm.

The sample 1902 may be mounted on a sample holder 1903. The sample holder 1903 may be configured to move or rotate the sample 1902. For example the sample holder 1903 may include a piezoelectric driver.

In an example shown in FIG. 15, the X-ray source 1901 may include one or more sub-sources (e.g., highly collimated X-ray beams). The sub-sources may be configured to illuminate portions of the sample 1902 and generate sub-images 1909 of these portions. One way to generate the sub-sources is by using a two-dimensional grating. The portions may be spatially non-overlapping with one another. The sub-images may be spatially non-overlapping with one another. The detector 100 may be configured such that its windows are aligned with at least some of the sub-images. The sub-sources (e.g., beams scanning) and the detector 100 may be moved in a way to capture a sub-image of every portion of the sample 1902. This configuration allows reduced exposure to X-ray by not illuminating a portion of the sample where an image of that portion is not to be captured by the detector 100.

The focusing optics 1904 may be a Fresnel zone plate. A Fresnel zone plate, like most refractive optics that can be used as the focusing optics 1904, has chromatic aberration. Therefore, focal lengths of the Fresnel zone plate are different for X-rays with different wavelengths or frequencies. In this case, the focal point 1905 is determined with respect to X-rays with a predetermined wavelength or a predetermined small range of wavelengths.

The focusing optics 1904 may be a focusing optics based on multi-reflections. In this case, the focal point 1905 is determined with respect to X-rays with all wavelengths of interest.

The sample 302 may be a piece of life organ or tissue, with a thickness of 100 μm or below. The sample 1902 may be placed close to the focal point 1905, either on the side closer to the detector 100, or on the side closer to the X-ray source 1901.

The detector 100 may be able to resolve energy of the incident X-ray photons but does not necessarily have that capability.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system comprising an X-ray source and an apparatus suitable for detecting X-ray,
    wherein the apparatus comprises an X-ray absorption layer and a mask;
    wherein the mask comprises a first window and a second window, and a portion between the first window and the second window;
    wherein the first and second windows are not opaque to an incident X-ray;
    wherein the portion is opaque to the incident X-ray;
    wherein the first and second windows are arranged such that charge carriers generated in the X-ray absorption layer by an X-ray photon propagating through the first window and charge carriers generated in the X-ray absorption layer by an X-ray photon propagating through the second window do not spatially overlap;
    wherein the first window and the second window are nearest neighbors;
    wherein the X-ray source comprises a first sub-source configured to illuminate a first portion of a sample and form a first sub-image of the first portion on the apparatus; and
    wherein the X-ray source comprises a second sub-source configured to illuminate a second portion of the sample and form a second sub-image of the second portion on the apparatus.

2. The system of claim 1, wherein the first portion and the second portion do not overlap spatially.

3. The system of claim 1, wherein the first sub-image and the second sub-image do not overlap spatially.

4. The system of claim 1, wherein the first window is aligned with the first sub-image and the second window is aligned with the second sub-image.

5. The system of claim 1, wherein the apparatus further comprises a first set of electrodes configured to receive a signal from the incident X-ray propagating through the first window, and a second set of electrodes configured to receive a signal from the incident X-ray propagating through the second window.

6. The system of claim 5, wherein receiving the signal comprises collecting charge carriers generated by the incident X-ray.

7. The system of claim 1, wherein the first window or the second window or both comprises a blind hole.

8. The system of claim 1, wherein the first window or the second window or both comprises a blind slot.

9. The system of claim 1, wherein the first window or the second window or both comprises a material different from a material of the portion.

10. The system of claim 1, wherein the mask comprises a metal.

11. A method of using the system of claim 1, comprising:
    capturing the first sub-image by scanning the first sub-image with the first window; and
    capturing the second sub-image by scanning the second sub-image with the second window.

12. A method of using the system of claim 1, comprising:
    capturing a sub-image of every portion of the sample by moving the first sub-source, the second sub-source and the apparatus relative to the sample.

* * * * *